United States Patent [19]

McClelland et al.

[11] Patent Number: 4,808,525
[45] Date of Patent: Feb. 28, 1989

[54] SITE SPECIFIC CLEAVAGE OF DNA

[75] Inventors: Michael McClelland, New York, N.Y.; Louis G. Kessler, Dallas, Tex.

[73] Assignee: University of Georgia Research Center, Athens, Ga.

[21] Appl. No.: 96,765

[22] Filed: Sep. 11, 1987

Related U.S. Application Data

[63] Continuation of Ser. No. 696,794, Jan. 31, 1985.

[51] Int. Cl.$^4$ .................. C12P 19/34; C12P 21/00; C07H 15/12; C12Q 1/60
[52] U.S. Cl. ........................................ 435/91; 435/68; 435/70; 435/172.3; 435/320; 435/6; 435/317.1; 935/1; 935/6; 935/10; 536/27
[58] Field of Search ............... 435/68, 70, 6, 71, 235, 435/172.3, 317, 91; 536/27; 935/110, 6

[56] References Cited

U.S. PATENT DOCUMENTS 4,419,446 12/1983 Howley et al. ............... 435/172.3

OTHER PUBLICATIONS

McClelland, M. et al., 1984, PNAS 81:983.
Geier et al. (1979), J. Biol. Chem. 254: 1408-13.
Nelson et al., (1984), Nucleic Acids Res. 12: 5165-73.
"Complementary Specificity of Restriction Endonucleases of Diplocuccus . . . " J. Mol. Bio. (1977), 114, 153-168, Sanford Lacks and Bill Greenberg.
The Journal of Biological Chemistry, vol. 254, No. 4, Issue of Feb. 25, pp. 1408-1413, 1979, Gail E. Geier and Paul Modrich.
J. Mol. Biol. (1978), 118, 27-47, "Use of Restriction Enzymes to Study Eukaryotic DNA Methylation: . . . " Adrian P. Bird and Edwin M. Southern.
"A DNA Methylase from Thermust Thermophilus HB8" J. Biochem 88, 737-747 (1980), Showbu Sato et al.
"Site-Specific cleavage of DNA at 8- and 10-Base--Pair Sequences" Proc. Nat'l. Acad. Sci., U.S.A. vol. 81, pp. 983-987, Feb. 1984 Biochemistry.
Nucleic Acids Research, vol. 9, No. 24 (1981), "Purification and Characterization of Two New Modification Methylases; . . . ".
Nucleic Acids Research, vol. 11, No. 1 (1983), "The Effect of Site Specific Methylation on Restriction Endonuclease Cleavage (update)".

Primary Examiner—Thomas G. Wiseman
Assistant Examiner—S. Seidman
Attorney, Agent, or Firm—Curtis, Morris & Safford

[57] ABSTRACT

The present invention provides a method for site-specific cleavage of double stranded DNA at sequences not less than eight base pairs long, comprising methylating he DNA with a sequence-specific methylase capable of recognizing and methylating a first sequence of the DNA, thereby generating a second sequence of the DNA capable of being recognized by a site-specific endonuclease, the first and second sequences having an overlapping part thereof; the length of the combined methylase and endonuclease recognition sites being not less than eight base pairs long, and cleaving the methylated DNA by treatment with the site-specific endonuclease. This method is useful for increasing the selectivity of cutting DNA stands using restriction endonucleases, thereby permitting the isolation of large DNA fragments and the generation of unique sites in DNA fragments, e.g., cloning vectors. Also provided is a DNA vector having a terminal sequence not less than eight base pairs long which can be recognized and cut by a site-specific endonuclease.

21 Claims, 3 Drawing Sheets

SITE SPECIFIC CLEAVAGE OF DNA

This application is a continuation of application Ser. No. 696,794, filed Jan. 31, 1985.

BACKGROUND OF THE INVENTION

This work was supported in part by grants from the National Institutes of Health.

1. Field of the Invention

The present invention relates to a method for site-specific cleavage of DNA at sequences not less than eight-base-pairs long, and particularly to a method comprising methylating the DNA with a sequence-specific methylase and cleaving said methylated DNA by treatment with a site-specific endonuclease enzyme.

2. Description of the Prior Art

In molecular biology, restriction endonucleases have proven to be extremely useful tools because of their ability to recognize specific sequences of DNA bases in double stranded DNAs and to cleave both DNA strands at these recognition sites. Because of this inherent ability, restriction endonucleases have provided a means for DNA mapping, sequencing and recombination in vitro. Type I restriction endonucleases recognize double-stranded DNA sequences up to 7 base pairs long but do not cleave site specifically. In contrast, type II restriction endonucleases have proved useful in molecular biology by virtue of their ability to recognize specific sequences of 4 to 6 bases in double-stranded DNA and cleave both strands at specific sites close to or in their recognition sequences (see, e.g., Roberts, R. J., Restriction and modification enzymes and their recognition sequences 11: r 135–167 (1983)).

The known recognition sites for restriction endonucleases, however, are only 4 to 7 base pairs long. Because of their short length, these sequences are likely to repeat themselves quite frequently in any one DNA strand. This phenomenon limits the selectivity activity which may be obtained in cutting specific DNA strands using restriction endonucleases by themselves.

More recently, DNA methylases were isolated. DNA methylases are site-specific enzymes which recognize a defined DNA sequence and methylate at one or more of the bases within the nucleic acid sequence (Sato, S.; Nakazawa, K.; and Shinomiya, T., "A DNA Methylase from T. thermophilus HB8", J. Biochem. 88: 737–747 (1980); Bird, A. P. and Southern, E. M., "Use of Restriction Enzymes to Study Eukaryotic DNA Methylation", J. Mol. Biol. 118: 27–47 (1978); McClelland, M., (III), "Purification and Characterization of two new Modification Methylases: M. Cla I from *C. latum L* and M. Taq I from *T. aquaticus* YTI", Nucleic Acids Res. 9(24): 6795–6804 (1981); and McClelland, M., (II) "The Effect of Site-Specific Methylation on Restriction Endonuclease Cleavage" (update), Nucleic Acid Res. 11(1): r169–r173 (1983)).

Many bacterial species have strain-specific enzymatic systems of DNA modification and restriction that serve as mechanisms for recognition and degradation of invading foreign DNAs. The essential enzymatic components of the systems are a modification enzyme that methylates the host DNA, and a restriction enzyme that recognizes as a foreigner and cleaves any DNA not carrying the host-specific methylation pattern. (McClelland, M., (I) "The Effect of Sequence-Specific DNA Methylation on Restriction Endonuclease Cleavage", Nucleic Acids Research 9(22): 5859–5866 (1981); Lacks, S.; and Greenberg, B., "Complementary Specificity of Restriction Endonucleases of *D. pneumoniae* with Respect to DNA Methylation", J. Mol. Biol. 114: 153–168 (1977); Geier, G. E., and Modrich, P., "Recognition Sequence of the dam Methylase of *E. coli* K12 and Mode of Cleavage of Dpn I Endonuclease", J. Bio. Chem. 254 (4): 1408–1413 (1979). McClelland, M., Kessler, L. G. and Bittner, M., "Site-specific Cleavage of DNA at 8- and 10-base pair Sequences", P.N.A.S. (USA) 81: 983–987 (1984), disclosing the present invention is however not considered prior art in view of its publication date.

Accordingly, there remained a need for more specific recognition sites which occur less frequently on each DNA strand, thereby affording higher selectivity in cutting DNA strands using restriction endonucleases.

SUMMARY OF THE INVENTION

The present invention provides a method for site-specific cleavage of DNA at sequences not less than 8 base pairs long, comprising methylating the DNA with a sequence specific methylase capable of recognizing and methylating a first sequence of the DNA, thereby generating an second sequence of the DNA capable of being recognized by a site-specific methylation-dependent endonuclease, the first and second sequences having an overlapping part thereof, the length of the combined methylase and endonuclease recognition sites being not less than 8 base pairs long, and cleaving the methylated DNA by treatment with the site-specific methylation-dependent endonuclease. This method is useful for increasing the selectivity of cutting DNA strands using restriction endonucleases, thereby permitting the isolation of large DNA fragments and the generation of unique sites in DNA fragments, e.g., cloning vectors.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings wherein.

Lanes:

A: M. Taq I-methylated Dpn I-digested pMON 2001;
B: M. Taq I-methylated, Bgl I-digested pMON 2001;
C: M. Taq I-methylated Dpn I/Bgl I-digested pMON 2001;
D: M. Taq I-methylated Dpn I/Bgl I-digested pMON 2002;
E: M. Cla I-methylated, Dpn I-digested pMON 2002;
F: uncut pMON 2002;
G: M. Cla I-methylated, Bgl I-digested pMON 2002;
H: M. Cla I-methylated Dpn I/Bgl I-digested pMON 2002;
I: M. Cla I-methylated Sph I-digested pMON 2001;
J: M. Cla I-methylated Dpn I/Sph I-digested pMON 2001;
K: Sph I/Cla I digested pMON 2001;
L: M. Cla I-methylated Dpn I-digested pMON 2001;
M: uncut pMON 2001;
N: M. Cla I-methylated Dpn I/Bgl I-digested pMON 2001;
O: Bgl I/Cla I-digested pMON 2001;

P: M. Cla I-methylated Dpn I-digested pMON 2002;
Q: M. Cla I-methylated Sph I-digested pMON 2002;
R: M. Cla I-methylated Dpn I/Sph I-digested pMON 2002;
S: Sph I/Cla I-digested pMON 2002.

Figure 2:
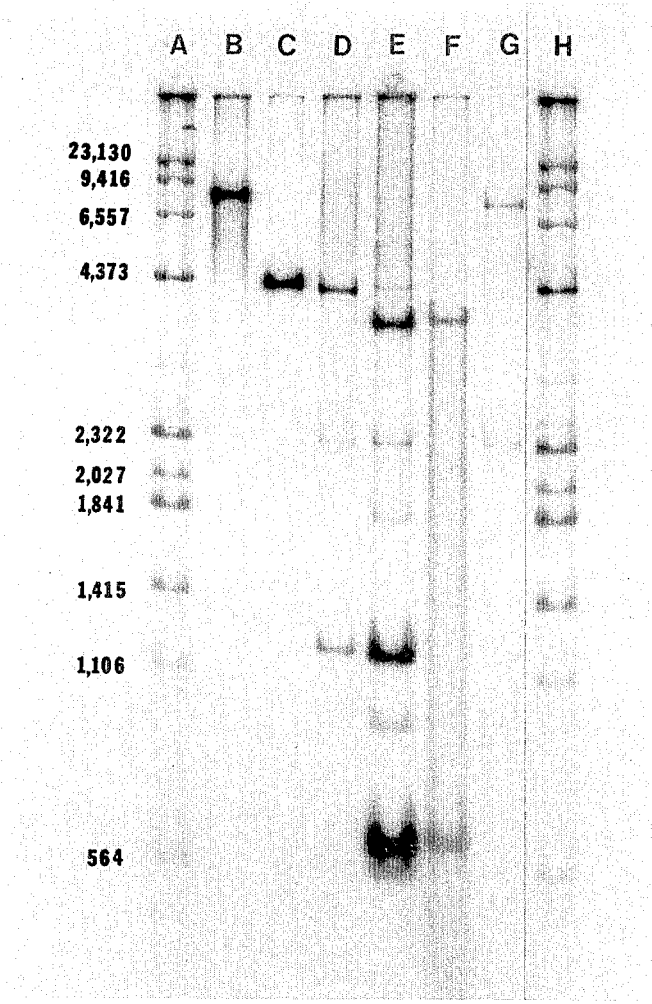

FIG. 2 represents a restriction of the pMON 2001 derivative pLK1. After restriction digestion of pLK1, fragments were end-labeled by using $\alpha^{32}P$ dCTP and electrophoresed through 1.5% agarose. DNA was visualized by autoradiography.

Lanes:

A and H: Hind III-digested phase lambda and Hinc II/Pvu II-digested pBR322 (molecular weight standards);
B: Hind III-digested pLK1;
C: Hind III-digested pMON 2002;
D: Hind III/EcoR I-digested pLK1;
E: Sal I/Eco RI-digested pLK1;
F: Sal I-digested pMON 2002;
G: Sma I/Eco RI-digested pMOB 45.

Figure 3:
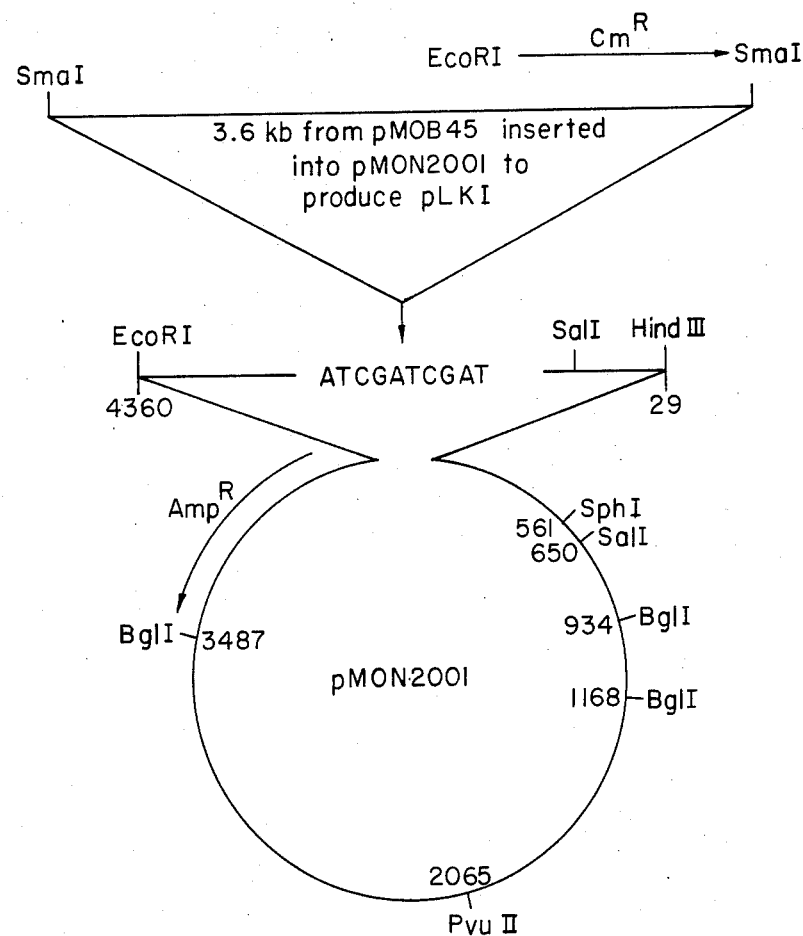

FIG. 3 represents a restriction map of pMON2001 and pLK1. Nucleotide positions of restriction endonuclease recognition sites are relative to the Eco R I site at 4360 in pBR322 (kb: Kilobases; Cm$^R$; chloramphenicol resistance; Amp$^R$: ampicillin resistance).

DESCRIPTION OF THE PREFERRED EMBODIMENTS

The present invention arose as the result of investigations into the possibility of recognizing and cutting infrequently found DNA sequences present in double stranded DNAs. Type I restriction endonucleases recognize double-stranded DNA sequences up to 7 base pairs long but do not cleave site-specifically. In contrast, type II restriction endonucleases have proved useful in molecular biology by virtue of their ability to recognize specific sequences of 4 to 6 bases in double-stranded DNA and cleave both strands at specific sites close to or in the recognition sequences.

The present invention relates to a more selective cleavage of double stranded DNA based on composite endonuclease recognition sequences which are at least 8 base pairs long. A composite recognition site is defined for the purpose of this application as a site made up of the combination of at least two non-identical, overlapping recognition sites. The greater length of these recognition sites makes them more infrequent in any one DNA strand and therefore renders their repetition less likely. Thus, fewer of these cleavage sites will exist on any one DNA strand and a more selective cutting of the double stranded DNA will be possible, thereby resulting in longer DNA fragments.

The following abbreviations will be used throughout the present Application.

A represents adenine; T represents thymine; G represents guanine and C represents cytosine; DNA represents deoxyribonucleic acid. (A/T) indicates that either A or T may occupy a particular position in the DNA sequence. $^mC$ and $^mA$ represent methylated C and A.

For the present description the term isoschizomer is defined as follows: isoschizomers are restriction endonucleases isolated from different strains but which have the same recognition sequence.

In the present invention, composite recognition sites are obtained by combining the action of two enzymes: a methylase and a restriction endonuclease. The two enzymes used have overlapping recognition sites and the use in combination of these two enzymes results in fact, in the formation of a composite recognition sites which are longer than could otherwise be obtained by using only one enzyme.

A strand of DNA is first treated with a methylase which modifies the double stranded DNA at specific recognition sites by methylation of one or more nucleotides on one or both strands. The DNA is then treated with a restriction endonuclease which is only able to cleave the double stranded DNA at sites which it both recognizes and which have been modified by the methylase. The combined use of these two enzymes greatly decreases the number of sites of a DNA fragment which are cleaved and thus makes a more selective cleavage of DNA possible.

In a particular application of the invention, a specific 8 base pair long site of double stranded DNA is cut by the combined action of M. Taq I (a methylase) and Dpn I (a restriction endonuclease). Methylation by M. Taq I at a direct repeat of the M. Taq I recognition sequence:

| | M. Tag I  M. Tag I | |
|---|---|---|
| 5' | T·C·G·A·T·C·G·A | 3' |
| 3 | A·G·C·T·A·G·C·T | 5' | produces a Dpn I cleavage site

| | Dpn I | |
|---|---|---|
| 5' | T·C·G·$^m$A·T·C·G·A | 3' |
| 3' | A·G·C·T·$^m$A·G·C·T | 5' |
| | Dpn I cleavage | |

In another application of the invention, a specific 10 base pair long site of double stranded DNA:

5' ATCGATCGAT 3' is cut by the sequential action of M. Cla I (a methylase) and Dpn I (an endonuclease).

Dpn I is a sequence-specific endonuclease, isolated from Diplococcus pneumoniae (as described by Lacks and Greenberg, supra), which cuts double-stranded DNA in both strands at a sequence 5' G-$^m$A-T-C 3'

3' C-T-$^m$A-G 5' to produce flush ends (see, Geier and Modrich, supra). This enzyme and its isoschizomers are different from other known DNA endonucleases in that they require methylation at adenine in both strands in order to cleave DNA.

Any sequence-specific methylase that recognizes a sequence overlapping the Dpn I recognition sequence and methylates at the correct adenine in the overlapping sequence could generate a Dpn I cleavage site. For instance, the dam product of E. coli methylates GATC at adenine in both strands as indicated by Dreiseikelmann, B., Eichenlaub, R., and Wachernagel, W., B.B.A. 562: 418–428 (1979), and thus DNA from dam+ E. coli is cleaved by Dpn I. In contrast, DNA from dam− mutants of E. coli is not cleaved by Dpn I.

In general, restriction-modification enzymes recognize the same sequences as the corresponding restriction endonucleases and protect these sequences from endonuclease cleavage by methylating DNA at adenine or cytosine (Roberts, R. J., (Nucl. Acid Res. 11: r1350-r168 (1983); Smith, H. O., and Nathans, D., J. Mol. Biol. 81: 419-423 (1973); McClelland, M., (I) Nucleic Acid Res. 9: 5859-5866 (1981)). Thus, a prokaryote that contains a restriction endonuclease that recognizes a sequence overlapping GATC by two or more base pairs may also contain a corresponding modification enzyme that methylates at adenine in the overlapping sequence. Restriction methylase-recognition sequences that overlap GATC by two or three base pairs are summarized in Table 1. (See, Roberts, supra.)

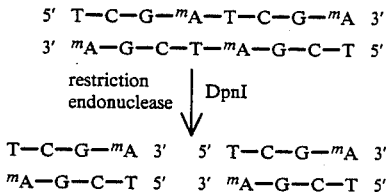

The 6 base pair sequence 5' TCGATC3', although containing the recognition sequences of both M. Taq I

TABLE 1

Type II restriction-modification methylases that recognize sequences overlapping GATC by two or three base pairs

| Methylase | Recognition Sequence | Dpn (Cleavage Sequence) |
|---|---|---|
| M. Taq I, m. Tth I | T—C—G—A | 5' T—C—G—$^m$A—T—C—G—$^m$A 3' <br> 3' $^m$A—G—C—T—$^m$A—G—C—T 5' |
| M. Cla I | A—T—C—G—A—T | 5' A—T—C—G—$^m$A—T—C—G—$^m$A—T 3' <br> 3' T—$^m$A—G—C—T—$^m$A—G—C—T—A 5' |
| M. Taq II* | G—A—C—C—G—A | 5' G—A—C—C—G—A—T—C—G—G—T—C 3' <br> 3' C—T—G—G—C—T—A—G—C—C—A—G 5' |
| M. Mbo II | G—A—A—G—A | 5' G—A—A—G—$^m$A—T—C—T—T—C 3' <br> 3' C—T—T—C—T—$^m$A—G—A—A—G 5' |
| M. Nru I* | T—C—G—C—G—A | 5' T—C—G—C—G—$^m$A—T—C—G—C—G—$^m$A 3' <br> 3' $^m$A—G—C—G—C—T—$^m$A—G—C—G—C—T 5' |
| M. Xba 1* | T—C—T—A—G—A | 5' T—C—T—A—G—$^m$A—T—C—T—A—G—$^m$A 3' <br> 3' $^m$A—G—A—T—C—T—$^m$A—G—A—T—C—T 5' |
| M. Eco B | T—G—A—N$_8$—T—G—C—T | A—G—C—A—N$_5$—T—G—A—T—C—A—N$_5$—T—G—C—T |
| M. Eco DXI | A—T—C—A—N$_7$—A—T—T—C | G—A—A—T—N$_5$—T—G—A—T—C—N$_5$—A—T—T—C |

| Methylase | Length (base pairs) | Comments |
|---|---|---|
| M. Taq I, m. Tth I | 8 | Methylation at T—C—G—$^m$A |
| M. Cla I | 10 | Methylation at A—T—C—G—$^m$A—T |
| M. Taq II* | 12 | |
| M. Mbo II | 10 | M. Mbo II methylates G—A—A—G—$^m$A (Nelson M., unpublished information) |
| M. Nru I* | 12 | |
| M. Xba 1* | 12 | Xba I does not cut T—$^{mC}$—T—A—G—A; thus, M. Xba I may methylate T—$^{mC}$—T—A—G—A |
| M. Eco B | 14 | Methylation at T—G—$^m$A—N$_8$—T—G—C—T |
| M. Eco DXI | 14 | |

*It is assumed that the methylase will recognize the same sequence as the corresponding restriction endonuclease. Dpn I cleavage sequences will be generated only if methylation occurs at the 3' adenine in the methylase recognition sequence. There are isoschizomers of many of these restriction systems. However, for simplicity only one example is given for each recognition sequence.

Three of these modification methylases, M. Taq I, M. Tth I, and M. Cla I, have been isolated and their methylation specificity has been determined (McClelland (III), supra; Sato, S., Nakazowa, K. and Shuromiya, T. J. Biochem. 88: 737-747 (1980).

Methylation by M. Taq I at a direct repeat of the M. Taq I recognition sequence (T-C-G-$^m$A) produces a Dpn I cleavage site:

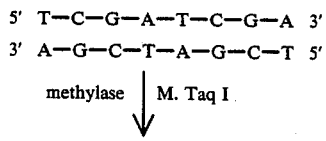

and Dpn I, would not be cleaved by Dpn I after M. Taq I methylation because the Dpn I recognition sequence would be methylated at adenine in only one strand:

5' T-C-G-$^m$A-T-C 3'

3' $^m$A-G-C-T-A-G 5'.

Methylation by M. Cla I at two partially overlapping M. Cla I recognition sequences produces a Dpn I cleavage site:

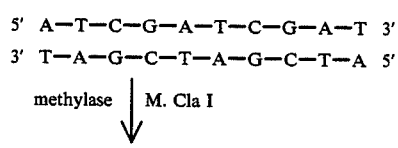

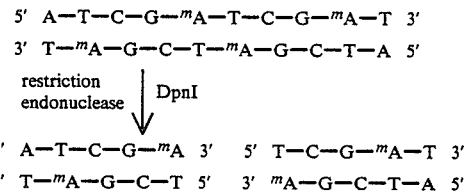

Thus, in DNA that is otherwise unmethylated at GATC, e.g., dam⁻ E. coli or mammalian DNA, the 8 and 10 base pair methylated sequences shown above would be the only Dpn I cleavage sites. The other potential 10 and 12 base-pair cleavage systems (see, Table 1) are described below.

A method for cutting specifically at the 8 base pair sequence TCGATCGA and the 10 base pair sequence ATCGATCGAT has been found and is disclosed herein.

In DNA that contains equal amounts of each base distribution at random, 8 and 10 base pair recognition sequences occur, on the average, approximately once every 65,000 ($4^8$) and 1,000,000 ($4^{10}$) base pairs, respectively. Furthermore, the sequences TCGATCGA and ATCGATCGAT contain two CG dinucleotides, which are known to occur one-fourth to one-fifth as frequently as expected from base composition in the DNA of higher eukaryotes and many of their viruses (Taylor, H. J., in "Molecular Genetics" Vol. 3: pp 89–116, ed. Taylor, H. J., Academic; N.Y., 1979; Salser, W. A., Cummings, I., Lui, A., Strommer, J., Padyatti, J. and Clarkie, P., in "Cellular and Molecular Switching, p. 621, eds. Stamatoyannopoulos G. and Nienhius, A. W., Grune and Stratton, 1979); McClelland, M., (IV) Nucleic Ac. Res. 10: 7865–7877 (1982); McClelland, M., (V) J. Mol. Evol. 19: 346–354 (1982)). Thus, the 8 base pair sequence TCGATCGA may occur as rarely as once in 1,000,000 base pairs and the 10 base pair sequence ATCGATCGAT only once in 16,000,000 base pairs in higher eukaryotic DNA. In contrast, type II restriction enzyme recognition sequences occur approximately once every 256 ($4^4$) to 1024 ($4^6$) base pairs.

The principle described here to generate Dpn I cleavage sites of 8 and 10 base pairs by M. Taq I or M. Cla I methylation can be used with other restriction methylases (See, for example, Table 1, supra). Examples of potential 10 base pair cleavage sites for Dpn I include inverted repeats of the recognition sequence for M. Hph I (GGTGATCACC) and M. Mbo II (GAAGATCTTC). Similarly, 12 base pair cleavage sites for Dpn I can be generated by direct repeats of the recognition sequence for M. Nru I (TCGCGATCGCGA) and M. Xba I (TCTAGATCTAGA).

Combinations of methylases will produce additional "hybrid" sites for Dpn I cleavage. For instance, a hypothetical M. Mbo II (GAAG$^m$A) methylase in combination with M. Cla I will generate Dpn I cleavage sites not only at the GAAGATCTTC and ATCGATCGAT sequences but also at the GAAGATCGAT and ATCGATCTTC sequences. Thus, the frequency of cleavage by both methylase/Dpn I systems simultaneously would be $4\times(\frac{1}{4})^{10}$, which is equivalent to the cleavage frequency of a restriction enzyme with a 9 base pair recognition sequence.

A number of applications for the technique described herein are possible.

The sequences TCGATCGA and ATCGATCGAT, in addition to being very rare, contain no stop or start codons in any frame. These sequences can be inserted as a unique cloning site in a self replicating DNA virus or plasmid, eliminating the necessity for further engineering to remove unwanted restriction sequences. The cloning vector may be of eukaryotic or prokaryotic origin, thereby being capable of replicating in eukaryotic, prokaryotic organisms or in both. Cloning vehicles can also be developed with ATCGATCGAT sequence flanking the usual cloning sites. Inserts into such vehicles could then be recovered intact by M. Taq I/Dpn I or M. Cla I/Dpn I cleavage. Suitable inserts are any double stranded DNA of eukaryotic or prokaryotic origin as well as synthetic double stranded DNA fragments, such as genomic DNA fragments and/or genes or fragments thereof. These inserts can be cloned into the vectors containing a terminus of this invention and thereafter cleaved by the corresponding site-specific endonuclease enzyme.

The cleavage of DNAs at 8 or 10 base pair recognition sequences also finds an application in the physical mapping of DNAs larger than 100,000 base pairs. Techniques are available for separating large DNAs (Fangman, W. L., Nucl. Ac. Res. 5: 653–665 (1978); Schwartz, D. C., Saffran, W., Welsh, J., Haas, R., Goldenberg, M., and Cantor, C. R., Cold Spring Harbor Syp. Quant. Biol. 47: 189–195 (1973)). For instance, an electrophoretic technique that can separate DNAs of up to 1,000,000 base pairs and differing in size by a few percent has recently been developed. This is achieved by the application of two-dimensional pulsed-field gel electrophoresis in 1% agarose gels. The method has already been used to separate yeast chromosomes (Schwartz et al, supra). Subsequently, genes can be probed by using Southern blotting (Southern, E. M., J. Mol. Biol. 98: 503–518 (1975)).

By using the pulsed-field gel electrophoretic method it is possible to detect a methylase/Dpn I fragment containing a gene by Southern blotting of methylase/Dpn I-digested total genomic DNA. λ Charon phage shotgun clones of this fragment can then be used for chromosome walking in the fragment containing the gene (Williams, B. and Blattner, F., in Genetic Engineering, Vol. 2, P. 201, eds. Setlow, J. K. Hollander, A., Plenun, N.Y. 1977)). One advantage of using such a fragment to construct λ phage libraries is to reduce the complexity of the DNA being probed in each step. This reduces the amount of phage to be screened and the problems encountered with regions of repetitive DNA.

This technique also allows chromosome walking from known genes in jumps of up to hundreds of kilobases. Genes are first identified in Southern blots of methylase/Dpn I restriction fragments of total chromosomal DNA. These fragments are then isolated and end fragments thereof subcloned. This can be achieved by ligating a linearized cloning vector to the isolated methylase/Dpn I fragment followed by cleavage with a site-specific restriction enzyme chosen which will not destroy the vector while reducing the size of the methylase/Dpn I fragment attached to the vector. Religation at low DNA concentration then leads to circularization of DNA.

Vectors with inserts may be primarily of two types, i.e., containing DNA extending from either end of the methylase/Dpn I fragment to the first restriction site in the fragment. These end fragments can in turn be used to probe a complete λ phage genomic bank in search of overlapping sequences. Appropriate phage clones are used to probe Southern blots of the methylase/Dpn I-digested total genomic DNA. In this manner, fragments adjacent to the one containing the gene would be detected. This process can then be repeated with subclones of the ends of these adjacent fragments.

It is also possible to study long-range heterogeneity in large genomes by using Southern blots (Southern, supra) of methylase/Dpn I-digested DNA, separated by 1% agarose pulsed-field gel electrophoresis (Schwartz et al, supra). Loss or gain of a methylase/Dpn I site and large deletions or insertions between closely related organisms may be detected over a range of many kilobases.

The techniques described here, by permitting site-specific cleavage of DNA at no less than 8 and 10 base pair sequences, significantly increases the ability of researchers to study large genomes, which was only possible until now through the laborious and repetitious separation and blotting of substantially smaller DNA fragments.

Other restriction enzymes which only cut methylated DNA are likely to be found. In fact isoschizomers of Dpn I have been found that also requires methylation for cleavage (Hurlin P. and Schildkraut I., unpublished results). Given that the assay for restriction enzymes is usually DNA from *E. coli* the most likely methylation specific enzymes to be found are those that overlap the methylation pattern of *E. coli* DNA. Thus, since *E. coli* DNA is methylated at GmATC and CmC(A/T)GG sequences, it can be expected that GmATC specific and CmC(A/T)GG specific endonucleases will be found. GmATC specific enzymes have already been found and there is one report of a CmC(A/T)GG specific enzyme, Apy I (Gruenbaum Y. et al., Nucleic Acids Res. 9: p2509, 1981). A CmC(A/T)GG specific system can be used in a manner identical to the methylase/Dpn I system described herein. Examples of potential recognition sequences are shown in Table 2, below.

J., Holder, S. B., and Gallupi, G. R., J. Am. Chem. Soc. 105: 661–663 (1983), incoprorated herein by reference.

Enzymes

Purification of M. Taq I from *Thermus aquaticus* YT1 and M. Cla I from *Caryophanon latum L* and conditions for DNA methylation with M. Taq I and M. Cla I were as described in McClelland, M., (III), Nucleic Ac. Res. 9: 6795–6804 (1981), incorporated herein by reference. Dpn I was purchased from Bethesda Research Laboratories (Bethesda, MD). Other restriction endonucleases and T4 ligase were purchased from New England BioLabs (Boston, MA). All restriction endonuclease digestions and ligations were carried out using the vendors' recommended conditions. The end-labeling conditions and autoradiographic techniques were as described by Lansman, R. A., Shade, R. O., Shapira, J. F., and Avise, J. C., J. Mol. Evol. 17: 214–226 (1981), incorporated by reference. *Escherichia coli* DNA polymerase I large fragment was purchased from New England Nuclear (Boston, MA). DNA sequence analyses were carried out using the dideoxy technique as described by Sanger, F., Coulson, A. R., Barrell, B. G., Smith, A. J. H., and Roe, B. A., J. Mol. Biol. 143: 161–178 (1980), incorporated herein by reference.

Transformation and Selection of pMON2001 and pMON2002 Recombinants

The transformation and plasmid purification procedures utilized herein were as described in Dagert, M., and Erlich, S. D., Gene 6: 23–28 (1979), and in Ish-Horowitz, D., and Burke, J. F., Nucleic Ac. Res. 9: 2983–2998 (1981), respectively, both incorporated herein by reference. Selection was carried out on Luria plates containing ampicillin at 20 µg/ml. Screening was carried out on Luria plates containing tetracycline at 20 µg/ml.

TABLE 2

| | Sequence specific methylases which overlap CCLGG and CCCGGG | |
|---|---|---|
| Enzyme | Recognition Sequence | Potential Cleavage Sequence CCLGG |
| Bsp R I | GGCC | GGCCLGGCC |
| Asu I | GGNCC | GGNCCLGGNCC |
| Nla I | GGNNCC | GGNNCCLGGNNCC |
| Ava II | GGLCC | GGLCCLGGLCC |
| Sdu I | GXGCVC | GXGCCCLGGGCVC |
| Hgi J II | GRGCYC | GRGCCCLGGGCYC |
| Hgi C I | GGRYCC | GGRYCCLGGYRCC |
| Acy I | GRCGYC | GRCGCCLGGCGYC |
| Apa I | GGGCCC | GGGCCCLGGGCCC |
| Aac I | GGATCC | GGATCCLGGATCC |
| Nar I | GGCGCC | GGCGCCLGGCGCC |
| Bst E II | GGTNACC | GGTNACCLGGTNACC |
| Sfi I | GGCCNNNNNNNGGCC | GGCCNNNNNGGCCLGGCCNNNNNGGCC GGCCNNNNNGGCCLGGNNGGCC |
| Hae I | LGGCCL | LGGCCLGGCCL |

*Many isoschizomers exist for most of these recognition sequences. Only one enzyme is named in each case. In the recognition sequences R = A or G; Y = T or C; L = A or T; X = not C; V = not G; N = A, C, G or T.

EXAMPLES

Chemicals

5-Bromo-4-chloro-3-indolyl β-D-galactoside and isopropyl thiogalactoside were purchased from Sigma (St. Louis, MO). α$^{32}$PdCTP was purchased from New England Nuclear (Boston MA). The oligonucleotide CCATCGATCGATGG was synthesized chemically by the method of Adams, S. P., Kavka, K. S., Wyker, E.

Bacterial Strains and Plasmids

*E. coli* strains GM33 dam-3 (Marinus, M. G., and Morris, N. R., J. Bacteriol., 114: 1143–1150 (1973)) and SK 1592 were provided by S. Kushner. JM103 (disclosed by Messing, J. and Vieira, J., Gene 19: 269–276 (1982)) was provided by S. Hollingshead. pMOB45 is a temperature-sensitive copy number-defective plasmid containing gene for chloramphenicol and tetracycline resistance disclosed in Bittner, M., and Vapnek, D., Gene 15: 319–329 (1981).

CONSTRUCTION OF PLASMIDS CONTAINING THE SEQUENCE ATCGATCGAT

A derivative of pBR322 was constructed containing the 10 base pair sequence ATCGATCGAT predicted to be a substrate for Dpn l cleavage after M. Cla l or M. Taq l methylation.

The oligonucleotide ATCGATCGAT was inserted by blunt-end ligation at the Sma I site of the bacteriophage M13 derivative mp8 (disclosed by Messing and Viera, supra), to produce phages mp1001 and mp2002, which contain one and two copies, respectively, of the oligonucleotide insert. These phage produced white plaques on JM103 in the presence of 5-bromo-4-chloro-3-indolyl β-D-galactoside and isopropyl thiogalactoside. The sequence of the insert was confirmed by the dideoxy sequence analysis method of Sanger et al, supra.

Plasmids pMON 2001 and pMON 2002 were derived from pBR322 by insertion of the EcoR I-Hind III region of mp2001 and mp2002, respectively, in place of the EcoR I-Hind III region of pBR322. Both plasmids contain the ampicillin-resistance gene of pBR322. The tetracycline-resistance gene has been inactivated by the insertion.

Generation of Dpn I Cleavage Sites by M. Taq I and M. Cla I Methylation

Plasmids pMON 2001 and pMON 2002 were prepared from the E. coli dam$^-$ strain GM33 described by Ish-Horowitz et al, supra, and by Marinus, and Morris, Supra. This strain lacks the G$^m$ATC-specific dam methylase, which in wild type E. coli creates Dpn I cleavage sites. Plasmids were methylated with M. Taq I or M. Cla I as described in McClelland, supra. It was found that M. Taq I methylation at all sites, including sites on other DNA's such as pBR322, occured about 3% as efficiently in the presence of pMON 2001 or pMON 2001 (data not shown). Destruction of the sequence ATCGATCGAT by Cla I digestion restored normal M. Taq I methylation efficiency at all other sites. The reason for this phenomenon is not understood, but it may be that the methylase has a higher affinity for direct repeats of its recognition sequence. Total methylation can be achieved by increasing the amount of methylase used, the incubation time, or both.

Figure 1:
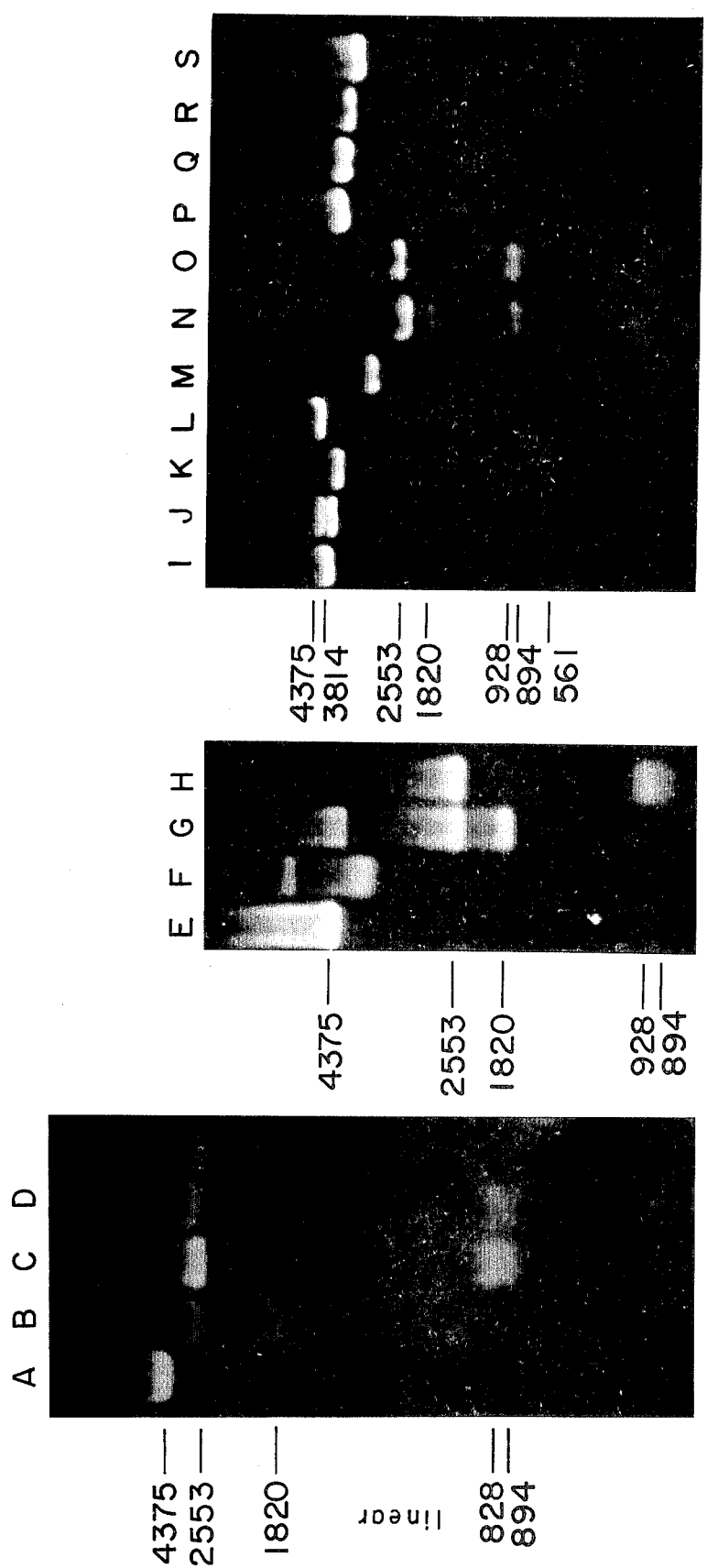
FIG. 1 depicts a gel electrophoresis of methylase/Dpn I cleavage sites in pMON 2001 and pMON 2002. Each lane contains 1 μg of DNA. Electrophoresis was conducted on 1% agarose gels.

As predicted, M. Taq I- and M. Cla I-methylated pMON 2001 and pMON 2002 were linearized by Dpn I. Restriction mapping showed Dpn I to cut specifically at a site in the Eco RI-Hind III insert of both plasmids (see FIG. 1). The plasmids contain 23 other occurrences of the sequence GATC, including partial overlaps with M. Taq I and M. Cla I at TCGATC, position 1127, and CGATCG, position 3735. None of these sequences is a substrate for Dpn I before or after methylation with M. Taq I or M. Cla I. This confirms previous observations that Dpn I requires methylation in both strands in order to cleave DNA (see, Lacks and Greenberg, supra and Gaier and Modrich, supra) and that under the reaction conditions used, M. Taq I and M. Cla I do not produce detectable methylation at subsets of their recognition sequences (see McClelland (III), supra).

Cloning at Methylase/Dpn I Sites

In order to demonstrate cloning at the 8 base pair Dpn I cleavage site produced by M. Taq I, a gene for chloramphenicol resistance was inserted at the M. Taq I/Dpn I site in pMON 2001; pMOB 45 was cleaved with Sma I to generate three fragments, one of which is 3.6 kilobases long and contains a chloramphenicol-resistance gene. This mixture was blunt-end ligated to M. Taq I/Dpn I-linearized pMON 2001 and transformed into SK 1592 (Dagert and Erlich, supra). Selection for ampicillin and chloramphenicol resistance and screening for tetracycline sensitivity were carried out. Ampicillin-resistant, chloramphenicol-resistant, tetracycline-sensitive colonies were picked and further screened by restriction mapping. Fragments were end-labeled using large fragment DNA polymerase I prior to electrophoresis (see FIG. 2). The 3.6 kilobase Sma I fragment of pMOB 45 containing the chloramphenicol-resistance gene maps to the region between the EcoR I and Sal I sites in the amp$^R$, cm$^R$, tet$^S$ recombinant plasmid pLKl, derived from pMON 2001 after M. Taq I/Dpn I cleavage (see, FIG. 3, and FIG. 1 (lanes D and E)). This corresponds to the 40 base pair region containing the direct repeats of Taq I recognition sequences.

Specific cutting and ligation at the 10-base-pair M. Cla I/Dpn I site was also demonstrated. Deletions of the region from the M. Cla I/Dpn I site to the Pvu II site at position 2067 in plasmids pMON 2001 and pMON 2002 were constructed (see, FIG. 3). M. Cla I-methylated pMON 2001 and pMON 2002 were each double digested with Dpn I/Pvu II and religated. The religated DNA was then redigested with Cla I/Pvu II/Ava I and then transformed into SK 1592 (see, Dagert and Ehrlich, supra). Cells were selected for ampicillin resistance and characterized by restriction digestion. Under such conditions, the majority of molecules expected to confer ampicillin resistance and remain in closed circular form were those in which the region containing the Ava I site at position 1424 had been deleted and in which the M. Cla I/Dpn I site was ligated to the Pvu II site. The five ampicillin-resistant pMON 2001-derived clones and the six pMON 2002-derived clones characterized by restriction analysis contained the expected deletion from the M. Cla I/Dpn I site to the Pvu II site (data not shown).

What is claimed as new and desired to be secured by Letters Patent of the United States is:

1. A method for site specific cleavage of a double-stranded DNA molecule at a recognition sequence not less than eight base pairs long, comprising:
   (a) contacting said double-stranded DNA molecule, which has a least two methylase recognition sequences, with at least one sequence specific methylase to produce a methylated double-stranded DNA molecule having a newly created DNA specific methylation dependent restriction endonuclease recognition sequence which partly overlaps with at least two of said methylase recognition sequences and said overlapping sequences having a combined length of not less than eight base pairs; and
   (b) contacting said methylated double-stranded DNA molecule with a methylation dependent DNA specific restriction endonuclease, under conditions sufficient for cleavage of the double-stranded DNA molecules by said restriction endonuclease.

2. A method for site specific cleavage of a double-stranded DNA molecule at a recognition sequence not less than eight base pairs long, comprising:
   (a) contacting said double-stranded DNA molecule, which has at least one methylase recognition sequence, with at least one sequence specific methylase, to produce a methylated double-stranded DNA molecule having a newly created DNA specific methylation dependent restriction endonuclease recognition sequence which partly overlaps with at least one of said methylase recognition sequences and said overlapping sequences have a combined length of not less than 8 base pairs, and (b) contacting said methylated double-stranded DNA molecule with a methylation dependent DNA specific restriction endonuclease, under conditions sufficient for cleavage of the double-stranded DNA molecule by said restriction endonuclease.

3. The method of claim 2 wherein the endonuclease is Dpn I, Apy I or isoschizomers thereof.

4. The method of claim 2, wherein the methylases are selected from the group consisting of M. Taq I, M. Tth I, M. Cla I, M. Hph I, M. Mbo II, M. Nru I and M Xba I, M Bsp R I, M Asu I, M Nla I, M Ava II, M Sdu I, M Hgi J II, M Hgi C I, M Acy I, M Apa I, M Aac I, M Nar I, M Bst E II, M Sfi I, M Hae I, M Eco B, M Eco DXI and methylases from isoschizomer systems thereof.

5. The method of claim 2 wherein
the endonuclease cleavage sequence(s) is (are) selected from the group consisting of
5' TCG$^m$ATCG$^m$A 3', 5' ATCG$^m$ATCG$^m$AT 3', 3' $^m$AGCT$^m$AGCT 5', 3' T$^m$AGCT$^m$AGCTA 5', 5' GGTG$^m$ATCACC 3', 5' GAAG$^m$ATCTTC 3', 3' CCACT$^m$AGTGG 5', 3' CTTCT$^m$AGAAG 5', 5' TCGCG$^m$ATCGCG$^m$A 3', 5' AGCAN$_5$TGATCAN$_5$TGCT 3', 3' $^m$AGCGCT$^m$AGCGCT 5', 3' TCGTN$_5$ACTAGTN$_5$ACGA 5', 5' TCTAG$^m$ATCTAG$^m$A 3', 5' GAATN$_7$TGATCAN$_7$ATTC 3', 3' $^m$AGATCT$^m$AGATCT 5', 3' CTTAN$_7$ACTAGTN$_7$TAAG 5', GGCCLGGCC, GGNCCLGGNCC, GGNNCCLGGNNCC, GGLCCLGGLCC, GXGCCCLGGGCVC, GRGCCCLGGGCYC, GGRYCCLGGYRCC, GRCGCCLGGCGYC, GGGCCCLGGGCCC, GGATCCLGGATCC, GGCGCCLGGCGCC, GGTNACCLGGTNACC, GGCCNNNNNGGCCLGGCCNNNNNGGCC, GGCCNNNNNGGCCLGGNNGGCC, and LGGCCLGGCCL;
R is A or G;
Y is T or C;
L is A or T;
N is A, C, G or T;
X is A, T or G; and
V is A, T or C.

6. The method of claim 2
wherein the methylase recognition sequence is selected from the group consisting of TCGA, ATCGAT, GGTGA, GAAGA, TCGCGA, TCTAGA, GGCC, GGNCC, GGNNCC, GGLCC, GXGCVC, GRGCYC, GGRYCC, GRCGYC, GGGCCC, GGATCC, GGCGCC, GGTNACC, GGCCNNNNNNGGCC, LGGCCL, TGAN$_8$TGCT, ATCAN$_7$ATTC; wherein
R is A or G;
Y is T or C;
L is A or T;
N is A, C, G or T;
X is A, T or G; and
V is A, T or C.

7. The method of claim 2 wherein the methylation occurs on one of the DNA strands.

8. The method of claim 2 wherein the methylation occurs on both DNA strands.

9. The method of claim 2 wherein the methylation occurs on A nucleotides.

10. The method of claim 2 wherein the methylation occurs on C nucleotides.

11. The method of claim 1 wherein the cleavage occurs at an 8 base pair sequence.

12. The method of claim 11 wherein the 8 base-pair sequence is TCGATCGA.

13. The method of claim 1 wherein the cleavage occurs at a 10 base pair sequence.

14. The method of claim 13 wherein the 10 base-pair sequence is ATCGATCGAT.

15. DNA vector having a double stranded DNA sequence of not less than 8 base pairs long selected from the group consisting of TCGATCGA, ATCGATCGAT, 5' TCG$^m$ATCG$^m$A 3', 5' ATCG$^m$ATCG$^m$AT 3', 3' $^m$AGCT$^m$AGCT 5', 3' T$^m$AGCT$^m$AGCTA 5', 5' GGTG$^m$ATCACC 3', 5' GAAG$^m$ATCTTC 3', 3' CCACT$^m$AGTGG 5', 3' CTTCT$^m$AGAAG 5', 5' TCGCG$^m$ATCGCG$^m$A 3', 5' AGCAN$_5$TGATCAN$_5$TGCT 3', 3' $^m$AGCGCT$^m$AGCGCT 5', 3' TCGTN$_5$ACTAGTN$_5$ACGA 5', 5' TCTAG$^m$ATCTAG$^m$A 3', 5' GAATN$_7$TGATCAN$_7$ATTC 3', 3' $^m$AGATCT$^m$AGATCT 5', 3' CTTAN$_7$ACTAGTN$_7$TAAG 5', GGCCLGGCC, GGNCCLGGNCC, GGNNCCLGGNNCC, GGLCCLGGLCC, GXGCCCLGGGCVC, GRGCCCLGGGCYC, GGRYCCLGGYRCC, GRCGCCLGGCGYC, GGGCCCLGGGCCC, GGATCCLGGATCC, GGCGCCLGGCGCC, GGTNACCLGGTNACC, GGCCNNNNNGGCCLGGCCNNNNNGGCC, GGCCNNNNNGGCCLGGNNGGCC, and LGGCCLGGCCL;
R is A or G;
Y is T or C;
L is A or T;
N is A, C, G or T;
X is A, T or G; and
V is A, T or C.

16. The DNA vector of claim 15 containing a self-replicating sequence of viral origin.

17. The DNA vector of claim 15 containing a self-replicating sequence of plasmid origin.

18. The DNA vector of claim 15 of eukaryotic origin.

19. The DNA vector of claim 15 of prokaryotic origin.

20. The DNA vector of claim 15 capable of replicating in an eukaryotic organism, a prokaryotic organism or in both.

21. A double stranded DNA comprising:
(a) the vector of claim 15, and
(b) a foreign DNA fragment cloned therein.

* * * * *